(12) United States Patent
Subramanian et al.

(10) Patent No.: US 11,690,584 B2
(45) Date of Patent: Jul. 4, 2023

(54) PROBE AND SYSTEM AND METHOD FOR DETECTING RADIATION AND MAGNETIC ACTIVITY FROM BODY TISSUE

(71) Applicant: BEST MEDICAL INTERNATIONAL, INC., Springfield, VA (US)

(72) Inventors: Manny R. Subramanian, Frederick, MD (US); Thomas M. Kraus, Smyrna, TN (US)

(73) Assignee: BEST MEDICAL INTERNATIONAL, INC., Springfield, VA (US)

( * ) Notice: Subject to any disclaimer, the term of this patent is extended or adjusted under 35 U.S.C. 154(b) by 323 days.

(21) Appl. No.: 15/957,783

(22) Filed: Apr. 19, 2018

(65) Prior Publication Data
US 2018/0303445 A1 Oct. 25, 2018

Related U.S. Application Data

(60) Provisional application No. 62/490,014, filed on Apr. 25, 2017.

(51) Int. Cl.
*A61B 5/05* (2021.01)
*A61B 6/00* (2006.01)
(Continued)

(52) U.S. Cl.
CPC .............. *A61B 6/4417* (2013.01); *A61B 5/05* (2013.01); *A61B 6/4057* (2013.01); *A61B 6/425* (2013.01);
(Continued)

(58) Field of Classification Search
CPC . A61B 6/4417; A61B 2562/0223; A61B 5/05; A61B 6/425; A61B 6/463;
(Continued)

(56) References Cited

U.S. PATENT DOCUMENTS

| 4,243,884 A | * | 1/1981 | Avera, Jr. | ............. | A61B 6/4057 |
| | | | | | 250/361 R |
| 4,801,803 A | * | 1/1989 | Denen | .................... | A61B 6/425 |
| | | | | | 250/336.1 |

(Continued)

FOREIGN PATENT DOCUMENTS

WO WO2065891 A2 8/2002

OTHER PUBLICATIONS

Oosterom et al., "Revolutionizing (robot-assisted) laparoscopic gamma tracing using a drop-in gamma probe technology", Jan. 30, 2016, American Journal of Nuclear Medicine and Molecular Imaging, pp. 1-17 (Year: 2016).*

(Continued)

*Primary Examiner* — Patricia J Park
*Assistant Examiner* — Adil Partap S Virk

(57) ABSTRACT

A hand-held probe for measuring radiation or magnetic activity includes a probe having a handle having a longitudinal axis and a shaft portion adapted to be inserted or held above a radiation or magnetic emitting source implanted within a patient's body or tissue of interest, the shaft portion includes a radiation or magnetic activity sensor configured to detect and measure radiation emitted from the radiation emitting source or magnetic activity from a magnetic source; the radiation emitting source being an implanted seed or a radioisotope that is injected near a tumor site in the patient's body; the probe including a signal processing device for further processing the measured radiation or magnetic activity; and a communication medium to exchange data from the hand-held probe with an external data processor unit.

21 Claims, 10 Drawing Sheets

(51) Int. Cl.
  *G01T 1/161* (2006.01)
  *G01R 33/02* (2006.01)
(52) U.S. Cl.
  CPC ............ *A61B 6/4258* (2013.01); *A61B 6/463* (2013.01); *A61B 6/5247* (2013.01); *A61B 6/563* (2013.01); *G01R 33/02* (2013.01); *G01T 1/161* (2013.01); *A61B 2562/0223* (2013.01)
(58) Field of Classification Search
  CPC ..... A61B 6/5247; A61B 6/563; A61B 6/4057; A61B 6/4258; A61B 1/00174; A61B 1/00183; A61B 17/7011; G01T 1/161; G01R 33/02
  See application file for complete search history.

(56) References Cited

U.S. PATENT DOCUMENTS

| | | | |
|---|---|---|---|
| 5,119,818 A | 6/1992 | Carroll et al. | |
| 5,170,055 A | 12/1992 | Carroll et al. | |
| 5,744,805 A | 4/1998 | Raylman et al. | |
| 5,846,513 A | 12/1998 | Carroll et al. | |
| 6,021,341 A * | 2/2000 | Scibilia | G01T 1/161 600/407 |
| 6,236,880 B1 * | 5/2001 | Raylman | A61B 6/4057 600/436 |
| 6,331,703 B1 | 12/2001 | Yamall et al. | |
| 6,771,802 B1 | 8/2004 | Patt et al. | |
| 7,561,051 B1 | 7/2009 | Kynor et al. | |
| 7,662,082 B2 | 2/2010 | White et al. | |
| 2004/0015075 A1 | 1/2004 | Kimchy et al. | |
| 2004/0162477 A1 * | 8/2004 | Okamura | A61B 5/415 600/409 |
| 2005/0197594 A1 | 9/2005 | Burbank et al. | |
| 2006/0184018 A1 | 8/2006 | Cox et al. | |
| 2007/0222467 A1 * | 9/2007 | Nickson | A61B 5/05 324/754.02 |
| 2009/0177082 A1 | 7/2009 | Baerwolff et al. | |
| 2009/0326371 A1 * | 12/2009 | McFerron | A61B 6/4258 600/436 |
| 2012/0032086 A1 | 2/2012 | Daghighian | |
| 2018/0235556 A1 * | 8/2018 | Speeg | G01T 1/202 |
| 2020/0196964 A1 * | 6/2020 | Speeg | G01T 1/244 |

OTHER PUBLICATIONS

International Search Report, Written Opinion of the International Searching Authority and Search History for PCT/US18/29168, dated Jul. 20, 2018, 13 pages.

European Search Report, including Written Opinion and Search Strategy, for corresponding EP Application No. 18791107, dated Nov. 26, 2020, 9 pages.

* cited by examiner

PROBE AND SYSTEM AND METHOD FOR DETECTING RADIATION AND MAGNETIC ACTIVITY FROM BODY TISSUE

CROSS REFERENCE TO RELATED APPLICATION

This application claims priority under 35 U.S.C. § 119 to U.S. Provisional Patent Application No. 62/490,014, filed on Apr. 25, 2017, hereby incorporated herein by reference in its entirety.

BACKGROUND OF THE INVENTION

1. Field of the Invention

The present invention relates generally to medical radiation or magnetic activity detection and quantitation in cancer therapy, and more particularly, to a hand-held medical radiation probe or a magnetic resonance probe, a radiation or magnetic activity detection system, and methods for detecting and quantifying radiation from an implanted radiation source or injected radioactive materials or for detecting magnetic activity from magnetic or paramagnetic materials proximal to a tumor for managing and treating it or to a tissue of interest.

2. Description of Related Art

Ionizing radiation is used medically in a wide range of therapeutic procedures and treatments. Brachytherapy techniques, involving the implantation of radioactive "seeds" in a defined array, often are used to deliver controlled doses of radiation to specific regions and parts of the body. Typically, a diseased organ or other to structure, such as a tumor, is the target of the applied radiation. For example, in the treatment of breast or prostate cancer, a prescribed number of radioactive seeds that serve to deliver controlled doses of radiation to the prostate are implanted at desired locations in the prostate. The brachytherapy can include locations in the prostate, breast, liver, head and neck, urethra, rectum, and other areas.

The use of radioactive materials to tag tissue within a patient for effecting its localization and demarcation by radiation detecting devices has been disclosed in the medical literature. Significant developments in the localization and demarcation of tissue bearing radioactive isotope tags for diagnostic and/or therapeutic purposes have occurred since that time. In fact, it is now becoming an established modality in the diagnosis and/or treatment of certain diseases, e.g., cancer, to introduce lymph node localizing agents tagged with a radioactive isotope (e.g., Technetium 99m, Indium-111, Iodine-123, and Iodine-125) into the body of the patient. Such radiopharmaceuticals tend to localize in particular tissue, such as the cancerous tissue, so that the gamma radiation emitted by the isotope agent can be detected by a radiation detector, e.g., a probe. In particular, the radiation detector or probe is disposed or positioned adjacent a portion of the patient's body where the cancerous tissue is suspected to be in order to detect if any radiation is emanating from that site. If the detector detects that radiation is emanating from that site, this indicates that cancerous tissue is likely to be found at that site.

Hand-held, radiation detecting probes particularly suitable for such cancer-finding applications have been disclosed previously. For example, U.S. Pat. Nos. 5,119,818 and 5,170,055, incorporated herein by reference in their entirety, disclose hand-held radiation detecting probes and accessories optimized to biopsy radiolabeled tissues. Additionally, U.S. Pat. No. 4,801,803 discloses a hand-held radiation detecting probe for use in immuno-guided surgery capable of detecting very faint gamma emissions and thereby localizing a cancerous tumor.

Moreover, U.S. Pat. No. 5,846,513, incorporated herein by reference in its entirety, discloses a percutaneously insertable radiation detecting probe, an associated analyzer, and a percutaneously insertable tumor removing instrument. The system is arranged to be used with a tumor localizing radiopharmaceutical. The radiation detecting probe includes a needle unit having a radiation sensor component therein and a handle to which the needle unit is releasably mounted.

For example, U.S. Patent Application Publication, US2006/0184018 A1, incorporated herein by reference in its entirety, discloses a hand-held gamma probe detector for the detection and location of an implanted radioactive seed during surgery. However, the aforementioned techniques have several disadvantages and typically lack the direct capability of imaging in-vivo and ex-vivo and improved probes and detection methods are needed.

In this regard certain radioactive materials migrate to nodes involved in tumor propagation. It is important to determine the presence of radiation in the nodes for surgical management. Thus, a gamma radioprobe and a method of detecting and assaying the dose of radiation near the cancerous target tissue, such as breast or prostrate, addressing the aforementioned problems is desired.

SUMMARY OF THE INVENTION

Embodiments of methods and apparatuses for a radiation probe to be used in the detection of radiation from cancer treatment and quantitating the radiation from an area of interest in a body or organism, such as a human, animal or reptilian body or other organism, are described, such as for human, veterinary or other biological diagnoses and treatments. Also described are embodiments of methods and apparatuses for a magnetic resonance probe to be used in the detection of magnetic activity from cancer treatment and quantitating the magnetic activity from an area of interest in a body or organism, such as a human, animal or reptilian body or other organism, are described, such as for human, veterinary or other biological diagnoses and treatments.

In an embodiment, an apparatus for measuring and quantifying the radiation or magnetic activity from an implant is described. The hand-held probe for measuring radiation or magnetic activity includes a probe having a handle having a longitudinal axis and a shaft portion adapted to be inserted or held above a radiation emitting source or a magnetic source implanted or located within a patient's body or tissue of interest, the shaft portion includes a radiation detector or radiation sensor configured to detect and measure radiation emitted from the radiation emitting source or includes a magnetic resonance detector configured to detect and measure magnetic activity emitted from the magnetic source; the radiation emitting source being a radiation an implanted seed or a radioisotope and the magnetic material is a magnetic or paramagnetic material that is injected or delivered near a tumor site or area of interest in the patient's body or tissue of interest; the probe including a signal processing device for further processing the measured radiation or the measured magnetic activity; and a communication medium to exchange data from the hand-held radioprobe with an external data processor unit.

In a further embodiment, the hand held radioprobe or magnetic resonance probe includes a detachable cover for the probe.

In another embodiment, a method for detecting the radiation or magnetic activity from an implant or tissue of interest is described. The method for detecting and measuring radiation using a radioprobe or for detecting and measuring magnetic activity using a magnetic resonance includes the steps of: identifying a tumor in a target tissue or organ to be treated in a patient or identifying a tissue of interest; disposing an implantable radioactive seed or magnetic particle-containing marker compound at the location near the tumor or tissue of interest; inserting a radioprobe or magnetic resonance probe near the proximity of the seed or marker; measuring the radioactivity by the radioprobe or measuring the magnetic activity by the magnetic resonance probe from the seed or marker based on distance of the seed or marker from the radioprobe or the magnetic resonance probe; transmitting radioactivity data or magnetic activity data from the measurement to a data processor by wireless communication or wired communication, such as by a cable, attached to the probe; quantifying the radioactivity or magnetic activity near the tumor or the tissue of interest; displaying the radiation or magnetic activity on a display device, such as a display meter, to determine the tumor status or the tissue of interest status, such as for the sentinel lymph nodes and the marker.

These and other features of the present invention will become readily apparent upon further review of the following specification and drawings.

DESCRIPTION OF THE DRAWINGS

Unless otherwise indicated, similar reference characters denote corresponding features consistently throughout the attached drawings.

DETAILED DESCRIPTION

Figure 1A:
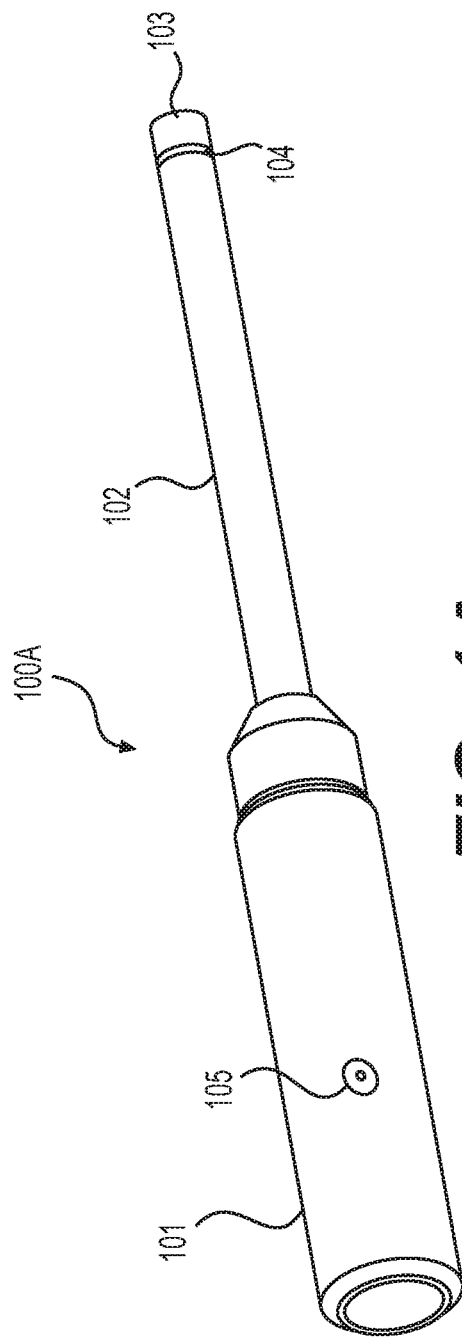
FIG. 1A is a perspective view illustrating a front face of an exemplary probe having a handle, such as a radioprobe having a radiation detector for detecting radiation or a magnetic resonance probe having a magnetic activity detector, according to the present invention.

The disclosure relates to apparatuses and methods of a medical device and methods for detecting and quantifying radiation from an implanted radiation source for treating cancer, or other diseased tissue, over a range and distance of targeted tissue, such as the breast or the prostrate areas. The exemplary embodiments of a radioprobe have both internal (in vivo) and external (ex-vivo) uses near the vicinity of the target tissue, particularly the breast and prostate, for example. Other target sites can include the liver, head and neck, urethra and rectum. Embodiments of the radioprobe and the radioprobe radiation detection system have applicability not only to humans, but to animals, reptiles and other organisms, as well, for example.

The hand-held probe for measuring radiation or magnetic activity, such as illustrated in FIGS. 1A, 1B, 2A, 2B and 3A, for example, to be further described, includes a probe having a handle having a longitudinal axis and a shaft portion adapted to be inserted or held above a radiation emitting source or magnetic source implanted within a patient's body or tissue of interest, the shaft portion including a radiation detector or sensor configured to detect and measure radiation emitted from the radiation emitting source or a magnetic resonance sensor to detect and measure magnetic activity from the magnetic source; the radiation emitting source is a suitable radiation emitting material, such as an implanted seed or a radioisotope, and the magnetic source is a magnetic or paramagnetic material, that is injected near or in a tumor site or near or in the tissue of interest, or other diseased tissue site, such as in the patient's body. One or more of the probe or the radiation or magnetic activity detection system includes a radiation processing device for receiving and further processing the detected measured radiation or includes a magnetic activity processing device for receiving and further processing the detected measured magnetic activity; and a communication device to exchange data from the hand-held probe with an external data processor unit, such as by wired or wireless communication.

Typically, the length of the shaft of the hand-held probe, such as a gamma radioprobe or a magnetic resonance probe, is from 3 cm to 210 cm, for example. The width of the probe shaft is typically in a range of from 1 mm to 5 cm, for example. The shaft of the hand-held probe, such as a gamma radioprobe, for measuring radiation, can include, for example, a plurality of radiation detectors, such as radiation sensors placed inside of the shaft portion for selectively detecting radiation, such as gamma radiation. Similarly, the shaft of the hand-held probe, such as a magnetic resonance probe, for measuring magnetic activity, can include, for example, a plurality of magnetic resonance detectors or sensors, such as placed inside of the shaft portion for selectively detecting the magnetic activity, such as magnetic flux density, magnetic flux, or magnetic field strength or intensity, for example. The hand-held probe, such as a gamma radioprobe for measuring radiation or a magnetic resonance probe for measuring magnetic activity, can further include a data communication device, or communication medium, to transmit measurement data to a computer, a laptop computer, a tablet or a cell phone device, for example. The communication device can be a direct coupled wired or a wireless communication medium or device, such as a device having Bluetooth capability, for example.

Figure 4A:
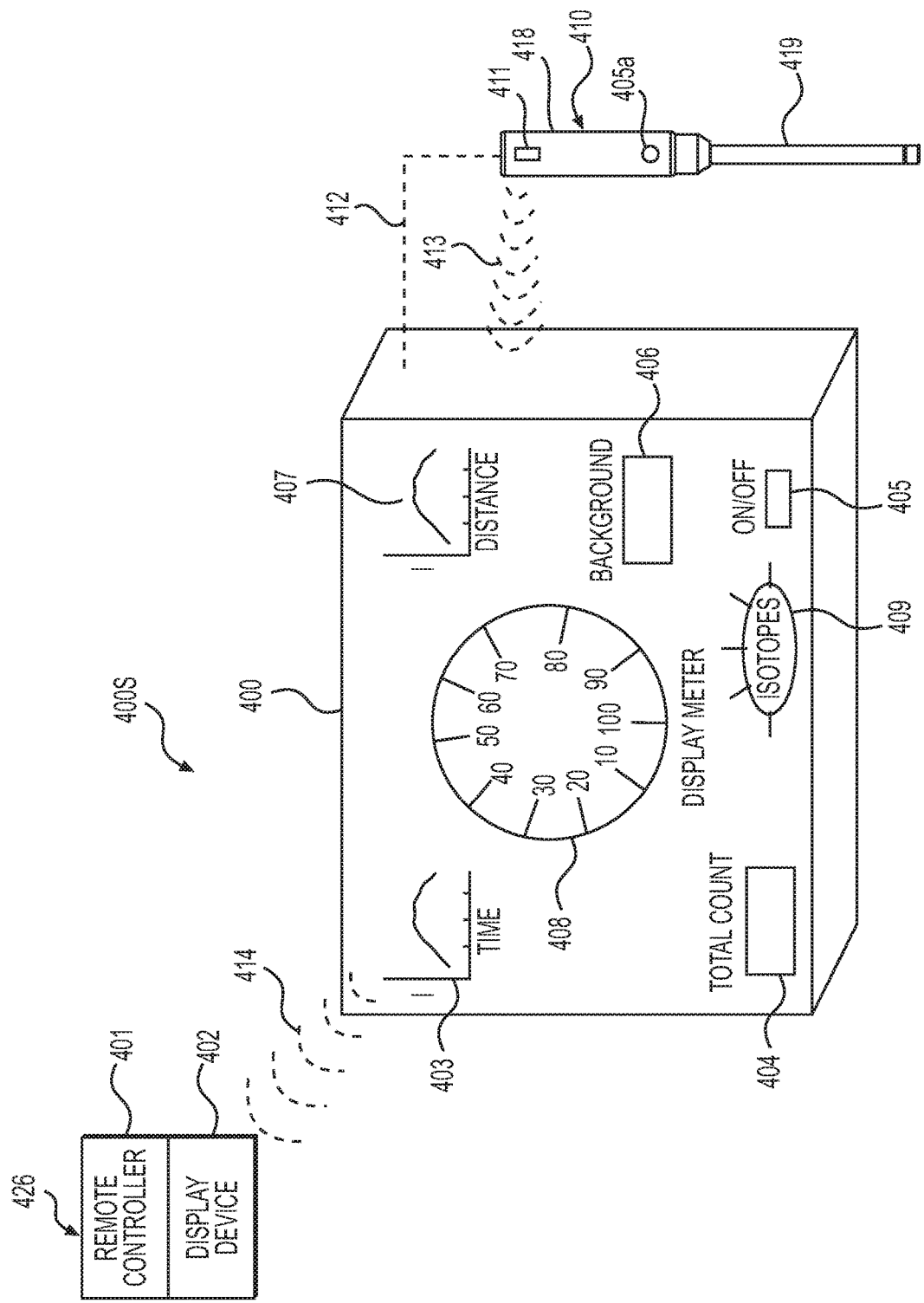
FIG. 4A shows a perspective view of an embodiment of a radiation or magnetic activity detection system including an exemplary embodiment of a graphical display of the activity (counts) versus time and activity (counts) versus distance of the measurement performed by a radioprobe, according to the present invention.
Figure 4B:
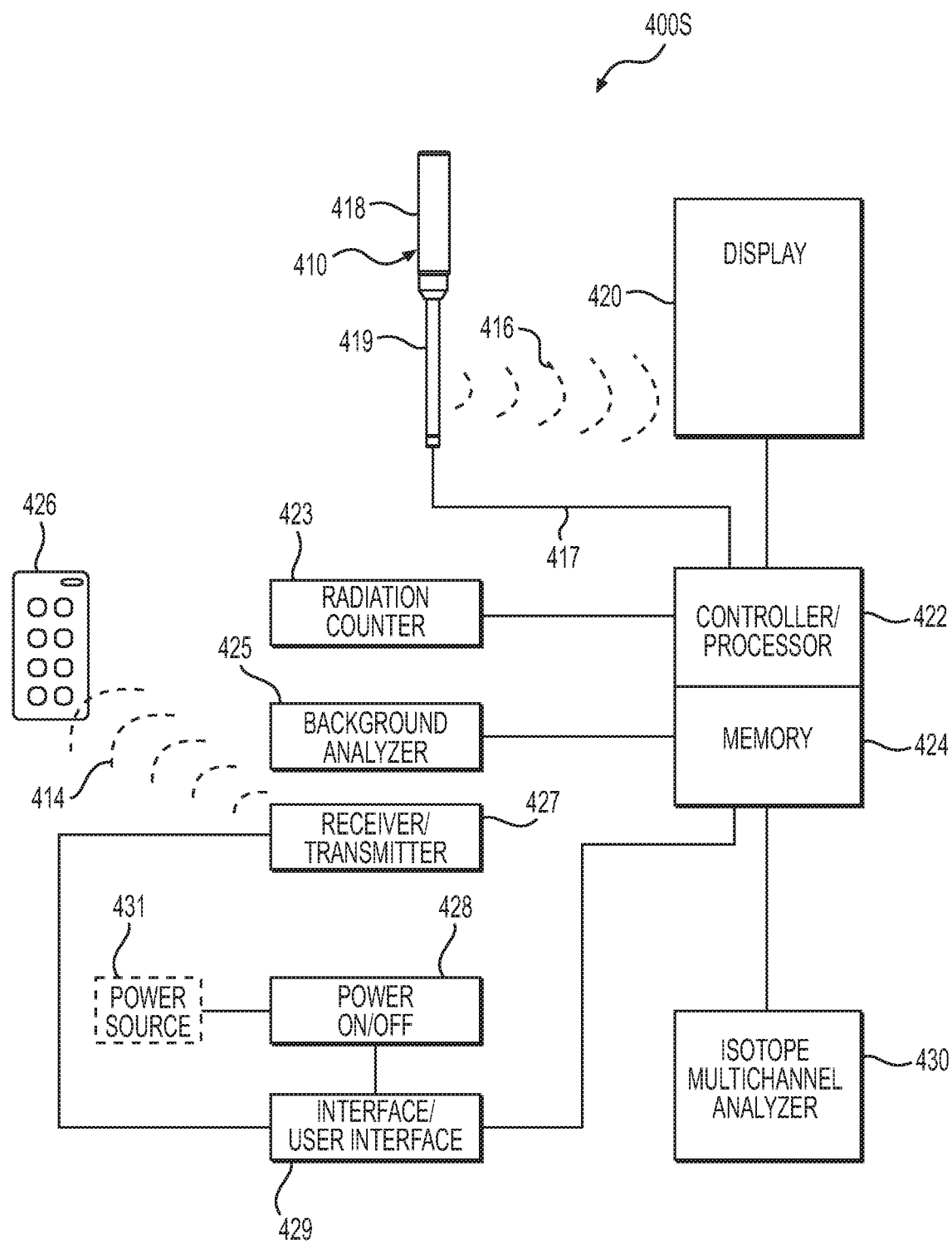
FIG. 4B shows the schematic perspective view of block diagram of the various components of an embodiment of a radiation or magnetic activity detection system for the detection, analysis and transmission of the radiation or magnetic activity detected by a probe, such as a radioprobe or a magnetic resonance probe, including components for wired or wireless transmission of the detected radiation or magnetic activity analysis or for analysis and display on a hand-held device, such as a cell phone, tablet, a laptop computer, or a computer, such as by Bluetooth or wireless or a wired transmission, according to the present invention.

The probe, such as a hand-held gamma radioprobe for measuring radiation or a magnetic resonance probe for measuring magnetic activity, and a radiation or magnetic activity detection system, such as illustrated in FIGS. 4A and 4B, to be further described, can further include a power supply device for the radiation detector(s) or the magnetic activity detector(s), such as for the radiation detectors or sensors or for the magnetic resonance detectors or sensors, for the signal processing device for analysis of the radiation detected or the magnetic activity detected by the probe and for a communication medium or communication device for receiving or transmitting information relating to the radiation detected or magnetic activity detected by the probe or relating to the analysis of the detected radiation or magnetic activity. The radiation detecting sensor for detecting radiation desirably is a MOSFET sensor, but can also be a semiconductor diode, scintillation counter, sodium iodide or other suitable compound for measuring the radioactivity counts, or other suitable detector or detection medium, as known to those skilled in the art and should not be construed in a limiting sense. The magnetic activity detector or sensor for detecting magnetic activity is desirably a magnetic resonance detector or sensor, or other suitable magnetic activity detector or sensor, as can detect various indicators of magnetic activity, such as magnetic flux density, magnetic flux, magnetic field strength or magnetic field intensity, for example, or can be other suitable detector or detection medium, as known to those skilled in the art and should not be construed in a limiting sense.

Figure 3A:
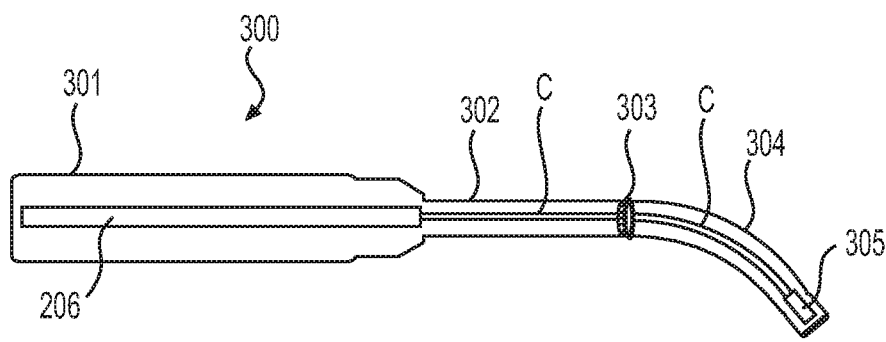
FIG. 3A shows a cross-sectional view of an embodiment of an exemplary probe, such as a radioprobe or a magnetic resonance probe, that includes a detachable probe which is curved to reach into a curved region inside the tissue, according to the present invention.

In another embodiment, a probe, such as a hand-held gamma radioprobe or a magnetic resonance probe, for measuring radiation or magnetic activity can further include a detachable substantially linear probe, such as illustrated in FIG. 3A, to be further described, or a detachable curved probe, such as illustrated in FIG. 3A, to be further described, configured to alter the angle of a tip of the probe in a range of from about 10° to 90° or from about 15° to 90°, for example, with respect to the longitudinal axis of the probe handle and to be rotated about the longitudinal axis to various angular positions.

The hand-held probe, such as illustrated in FIGS. 1A, 1B, 2A, 2B and 3A, for example, such as a gamma radioprobe for measuring or detecting radiation or a magnetic resonance probe for detecting magnetic activity, and the radiation or magnetic activity detection system according to the present invention, can also include a report unit or receiving device to provide feedback to a user, wherein the feedback includes information associated with the intensity of the radiation source detected, such as gamma radiation from a gamma radiation source, or information associated with the magnetic activity detected. The probe, such as a hand-held radioprobe, can be used to detect radiation from various radiation sources, such as wherein the radiation emitting source produces emissions of one or more radiation types selected from the group consisting of alpha rays, beta rays, gamma rays, x rays, and neutrons, for example. Also, the probe, such as a hand-held magnetic resonance probe, can be used to detect magnetic activity from various magnetic or paramagnetic sources or materials, such as magnetic or paramagnetic particles including nickel, cobalt or iron, or iron oxides, for example.

The probe, such as a hand-held gamma radioprobe or a magnetic resonance probe, such as illustrated in FIGS. 1A, 1B, 2A, 2B and 3A, for example, can have a housing material for the probe shaft that can be made from various suitable materials, such as a material selected from the group consisting of a polymeric material, glass, silicone, stainless steel, tungsten, copper, titanium and an alloy thereof, for example.

As used herein the term "brachytherapy" refers to the treatment of cancer, especially breast cancer or prostate cancer, by the insertion of radioactive implants directly into the tissue.

The following examples are provided by way of illustration to further illustrate exemplary probes, radiation or magnetic activity detection systems, and methods for detecting radiation around a radiation source or for detecting magnetic activity from a magnetic source near a tumor target or other diseased tissue or near tissue or an organism of interest, but are not intended to limit the probes, the radiation or magnetic activity detection systems, and the methods for detecting radiation or magnetic activity within the scope of the disclosure, and, therefore, should not be construed in a limiting sense.

Figure 1B:
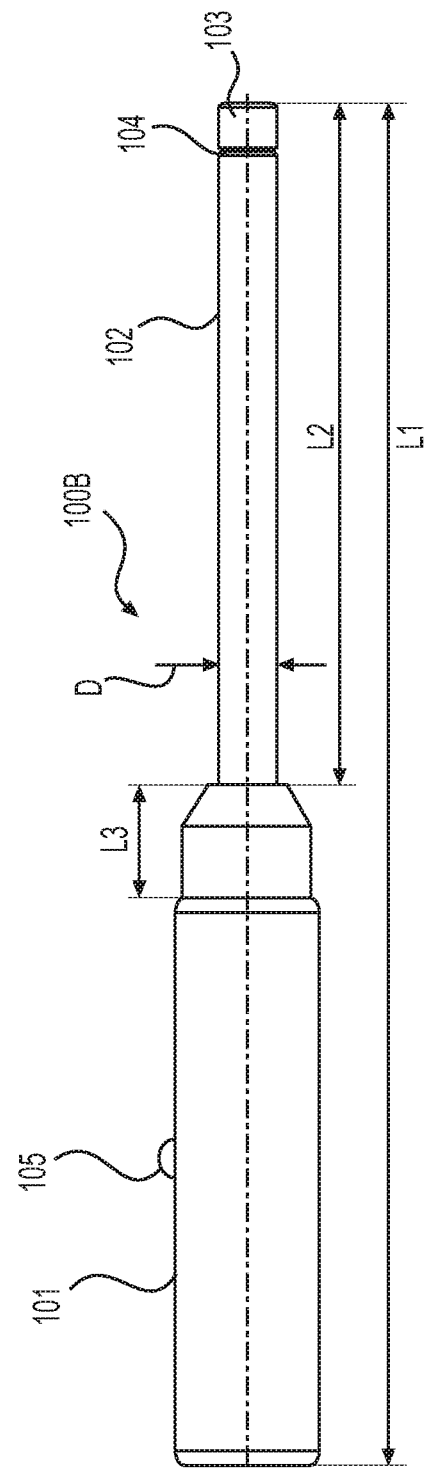
FIG. 1B shows exemplary relative dimensions of a probe, such as a radioprobe or a magnetic resonance probe, according to the present invention.

Referring to the figures, FIG. 1A shows the top perspective view illustrating a front face of an exemplary probe 100A having a handle portion 101 (hand-held portion) and a longitudinal radioprobe portion 102 in communication with the handle portion 101 and having a detector tip portion 103 and a tip connector 104. FIG. 1B shows a cross sectional view of a probe 100B having a handle portion 101 for a hand grip and a probe shaft 102 in communication with the handle portion 101 and including a detector 103 for detecting radiation emitted from an implant or a radio nuclide or for detecting magnetic activity from a magnetic source injected near a tumor tissue or near a tissue or organism of interest, according to the present invention. The probe length "L1" can typically be up to 210 cm, for example. The length of the probe portion "L2" of the longitudinal portion generally can be in a range of about 3 cm to 70 cm, for example, and can have various sizes of the detector tip portion 103 as can connect to the tip connector 104, such a detachable probe of suitable length. The length L2 of probe portion 102 can be selectively adjusted in length, as depend on the use or application, so that the length can also be extended generally in a range of up to around approximately 210 cm, as well as the length can be appropriately reduced. A diameter "D" of the rod or the shaft portion forming the probe portion 102 of the probe 100A, 100B can be anywhere in a range of from about 1 mm to about 5 cm, for example, but can be of various suitable diameters, as can depend on the use or application. A longitudinal axis of the probe is illustrated in FIG. 1B in the form of the short and long dashed line running through the center of the handle portion 101 and the longitudinal probe portion 102 having a detector tip portion 103. The probe material forming the probe portion 102, can be made of various suitable materials, such as plastic, metal, silicone, ceramic or glass, but can be of other various suitable materials, as can depend on the use or application. An ON/OFF switch, indicator or button 105, to indicate or control the power-on and power-off states to the probe, such as the probes 100A, 100B can be desirably included with the probe, as well.

Figure 2A:
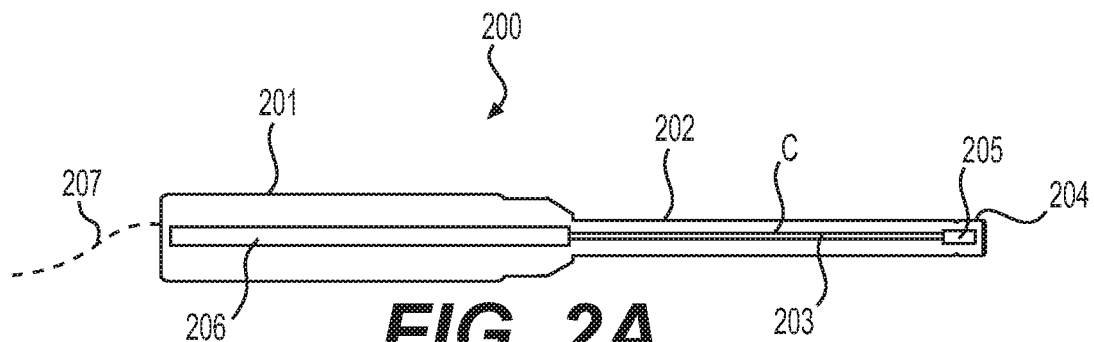
FIG. 2A shows a cross-sectional view of an embodiment of probe, such as a radioprobe including a metal-oxide-semiconductor field-effect transistor (MOSFET) or a magnetic resonance probe including a magnetic resonance detector, incorporated within the tip of the probe, according to the present invention.

FIG. 2A shows a transverse sectional view of a probe 200, such as a gamma radioprobe or a magnetic resonance probe, having a handle portion 201, a probe shaft portion 202 in communication with the handle portion 201, the probe shaft portion 202 including a sensor or detector 205, such as a radiation detector or sensor being a metal-oxide-semiconductor field-effect transistor (MOSFET) 205 or a magnetic resonance detector or sensor 205 to detect magnetic activity, within a tip portion 204 of the of the probe shaft 202, according to the present invention. The detected radiation measurement or signal or magnetic activity detected by the detector or sensor 205 is communicated or relayed via internal electronic wires into a signal receiving and processing unit 206. The signal receiving and processing unit 206 can process or pre-process the detected radiation or magnetic activity received from the sensor or detector 205 via a wired or wireless communication channel or medium "C" to provide the desired measurements or radiation or magnetic activity indications or other information, such as position or location information for the radiation source or magnetic source detected, as well as can communicate the detected measurement or the processed or pre-processed information to other components of the radiation or magnetic activity detection system, such as by wired or wireless communication, indicated by the numeral 207, such as illustrated in FIGS. 4A and 4B, to be described, for example.

Figure 2B:
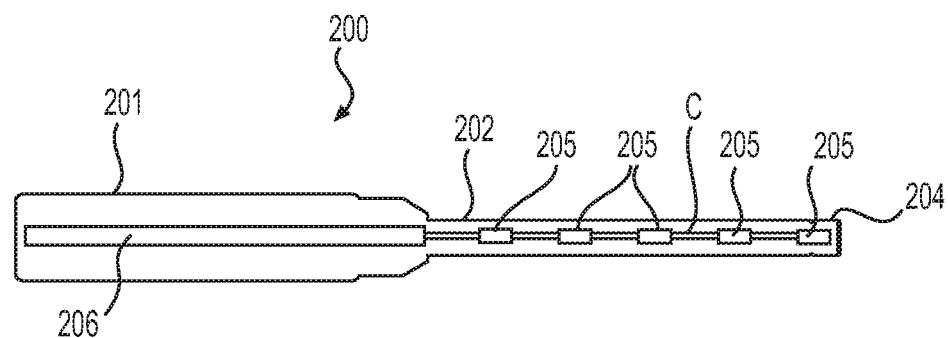
FIG. 2B shows a cross-sectional view of an embodiment of a probe, such as a radioprobe or a magnetic resonance probe, including a plurality of (five in the figure) detectors, such as metal-oxide-semiconductor field-effect transistors (MOSFETs) or magnetic resonance detectors, positioned within the body and tip of the probe, according to the present invention.

FIG. 2B shows a transverse sectional view of the probe 200, such as a gamma radioprobe or a magnetic resonance probe, having a handle portion 201 in communication with the probe shaft 202, the probe 200 including a plurality (typically about five) detectors or sensors 205, such as metal-oxide-semiconductor field-effect transistor (MOSFETs) 205 for detecting radiation or magnetic resonance detectors or sensors for detecting magnetic activity, positioned within the body of the probe shaft 202, including one detector or sensor 205 at the tip portion 204 of the probe 201, according to the present invention. The plurality of sensors or detectors 205 can detect radiation or magnetic activity and provide to the signal receiving and processing unit 206 detected radiation or magnetic activity information to process or pre-process the detected radiation or magnetic activity information received via the wired or wireless communication channel or medium "C" as can enable detection of, measurement of and location of one or more positions of radiation source or a magnetic source in tissue, according to the present invention.

FIG. 3A shows a transverse sectional view of an exemplary probe 300, such as a gamma radioprobe or a magnetic resonance probe, having a handle portion 301 and a longitudinal shaft portion 302 in communication with the handle portion 301. The probe shaft portion 302 has a curved detachable probe 304 connected via an attachment device 303, such as a screw cap mechanism 303 or a groove arrangement having mating grooves in the end of shaft portion 302 and at the end of the detachable probe 304 for selectively engaging and disengaging the shaft portion 302 and the detachable probe 304 with each other. The detachable probe 304 can include one or more sensors or detectors 305, such as one or more metal-oxide-semiconductor field-effect transistors (MOSFETs) 205, 305 to detect the radiation or one or more magnetic resonance detectors or sensors 205, 305 to detect magnetic activity, as described with respect to FIGS. 2A and 2B, and provide radiation detection information or magnetic activity information to signal receiving and processing unit 206, via a wired or wireless communication channel or medium "C", to process or pre-process the detected radiation information received from the one or more radiation sensors or radiation detectors 305 or to process or pre-process the detected magnetic activity information received from the one or more magnetic resonance sensors or magnetic resonance detectors 305. The detachable probe 304 can have a substantially linear configuration or a curved configuration, a curved configuration for the detachable probe 304 being illustrated in FIG. 3A, for example, The angle that is formed in and by the detachable probe 304 having a curved configuration can be suitably formed in an angular range of from about ten degrees (10°) to about 90 degrees (90°) or can be other suitable angle or curved configuration, as can depend on the use or application, as can be needed to reach the vicinity of a radiation emitting source, such as an implanted radioactivity seed or the radioactive source, or as can be needed to reach a magnetic source, in a body or tissue of interest, for example. The curved detachable probe 304 can be configured to alter the angle of the tip thereof, such as from 10° to 90°, with respect to the longitudinal axis (see, FIG. 1B) of the handle portion 301 so as to enable the probe 300 to be rotated about the longitudinal axis to various angular positions to position the probe for a procedure or measurement.

Figure 3B:
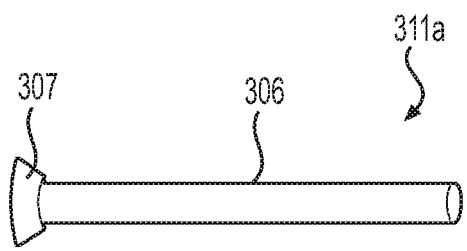
FIG. 3B shows a perspective view of an embodiment of an exemplary sterile detachable probe cover to be fitted over the probe, as can have a fixed probe or detachable probe, such as the probes illustrated in FIGS. 1A and 3A, according to the present invention.

FIG. 3B shows a transverse sectional view of an exemplary sterile detachable probe cover 311a having a lumen type shaft 306 having an opening end 307 for engaging with and being positioned over one or more of at least part of a shaft portion having a fixed probe, such as the probe shaft portion 202 of FIG. 2A, or positioned over all or part of a shaft portion of a probe having a detachable probe, such as over all or part of the shaft portion 302 including a detachable probe, such the curved detachable probe 304, connected via the attachment device 303, according to the present invention. The sterile probe cover 311a can be a semi-rigid or a flexible or elastic type probe cover made of suitable material to facilitate engagement with and positioning on various types and configurations and shapes of probes, as can depend on the use or application, and should not be construed in a limiting sense.

In various embodiments of probes, such as those of FIGS. 1A, 2A, 2B, and 3A, a suitable length of a tubing of a suitable material, such as a flexible catheter, can be positioned between the shaft portion and the probe portion of the probe that includes the one or more radiation detectors sensors 205, 305 or that includes the one or more magnetic resonance detectors or sensors 205, 305, with suitable connectors to communicatively connect the shaft portion, the tubing and the probe portion, and such use of a suitable material, such as a flexible catheter, can facilitate the probe being placed in various areas or portions of a body to enable radiation detection or magnetic activity detection in the body area or body portion. The detectors or sensors 205, 305 being suitable communicatively connected with a signal receiving and processing unit of the probe, such as the signal receiving and processing unit 206 for the receiving and processing of information related to the radiation or the magnetic activity detected, as described.

Figure 3C:
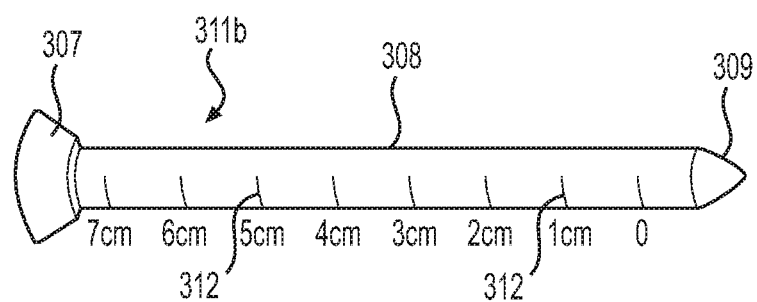
FIG. 3C shows a transverse sectional view of an embodiment of an exemplary sterile detachable probe cover to be fitted over a probe as can have a fixed probe or detachable probe, such as the probes illustrated in FIGS. 1A and 3A, having a measurement marked up length and tapered end, according to the present invention.

FIG. 3C shows a perspective view of an exemplary sterile detachable probe cover 311b as can be used with various embodiments of probes, such as the probes of FIGS. 1A, 2A, 2B, and 3A, for example. The probe cover 311b has a lumen type shaft 308 having an opening 307 as can be suitably connected with a probe shaft or fixed or detachable probe, as described. Along the length of the shaft 308 are provided a plurality of measurement gradations 312, as can have one or more a sensors or detectors 205, 305 positioned in association therewith for radiation or magnetic activity detection and for providing information as to the detected radiation or magnetic activity, such as a position, location, length or area of the detected radiation source or of the magnetic source. The probe cover can have a tapered end 309 to facilitate entry into a body and positioning of the probe in the area of a body for the radiation or magnetic activity detection measurement, according to the present invention.

Figure 3D:
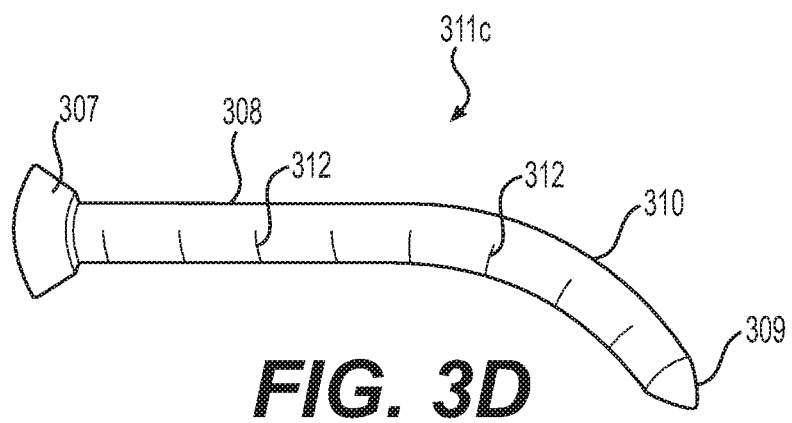
FIG. 3D shows a perspective view of an embodiment of an exemplary sterile detachable probe cover, as can have a fixed probe or detachable probe, such as the probes illustrated in FIGS. 1A and 3A, having a measurement marked-up length and having a tapered end, according to the present invention.

FIG. 3D shows a perspective view of an exemplary sterile detachable probe cover 311c, similar to the probe cover 311a, having an opening 307, a longitudinal lumen type shaft 308 having along the length of the shaft 308 a plurality of measurement gradations 312, as can have one or more sensors or detectors 205, 305 positioned in association therewith for radiation or magnetic activity detection and for providing information as to the detected radiation or detected magnetic activity, such as a position, location, length or area of the detected radiation source or magnetic source, as described. The probe cover 311c has, in addition to a length measurement gradation, a curved portion 310 to facilitate conforming or fitting the probe cover 311c to a curved probe end shape. The curved portion 310 is adjacent to a tapered end 309, as can facilitate placing the cover on a curved probe shaft and can facilitate entry and positioning of the probe in the area of the body for radiation or magnetic activity detection, as described, according to the present invention.

Figure 3E:
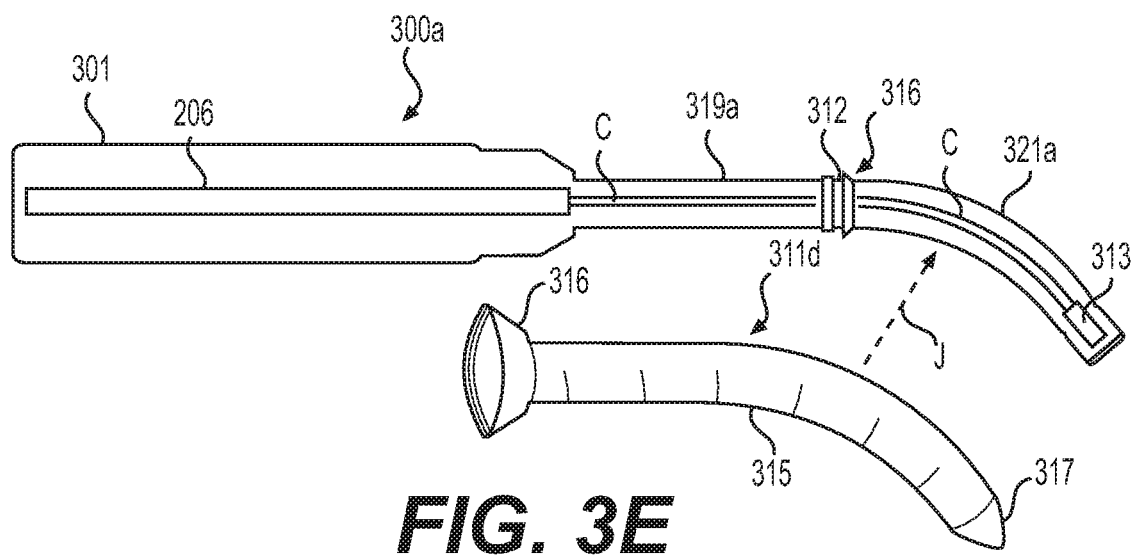
FIG. 3E shows a cross-sectional view of an embodiment of an exemplary sterile detachable probe cover to be attached to a probe and an exemplary probe, as can have a fixed probe or detachable probe, such as the probes illustrated in FIGS. 1A and 3A, having the probe cover attached thereto, the probe cover being attached to the probe by a slide on mechanism that slides on to the probe, according to the present invention.

FIG. 3E shows a transverse sectional view of an exemplary sterile detachable probe 300a, similar to probe 300 as described with respect to FIG. 3A. The probe 300a includes a handle portion 301, a shaft portion 319a in communication with the shaft portion 301, and a curved rod probe portion 321a connected to the shaft portion 319a at an attachment mechanism 312 and a sensor or detector 313 similar to the sensor or detector 205, 305, as described with respect to FIGS. 2A, 2B and 3A to detect radiation or magnetic activity. The probe shaft portion 319a has the curved detachable rod portion probe 321a connected via the attachment mechanism 312, such as by a slide on the attachment mechanism 312. The curved rod detachable probe portion 321a can include one or more sensors or detectors 313, such as one or more metal-oxide-semiconductor field-effect transistors (MOSFETs) 205, 305 to detect the radiation or one or more magnetic resonance detectors or sensors 205, 305 to detect magnetic activity, as described with respect to FIGS. 2A, 2B and 3A, and provide radiation or magnetic activity detection information to the signal receiving and processing unit 206, via a wired or wireless communication channel or medium "C", to process or pre-process the detected radiation or magnetic activity information received from the sensor or detector 313. The curved rod detachable probe portion 321a can have a substantially linear configuration or a curved configuration, a curved configuration for the detachable probe portion 321a being illustrated in FIG. 3E, for example. The angle that is formed in and by the detachable rod probe portion 321a having a curved configuration can be suitably formed in an angular range of from about ten degrees (10°) to about 90 degrees (90°) or can be other suitable angle or curved configuration, as can depend on the use or application, or as needed to reach the vicinity of the implanted radioactivity seed, the radioactive source or magnetic source in a body or a tissue of interest, for example. The curved rod detachable probe portion 321a can be configured to alter the angle of the tip thereof, such as from 10° to 90°, with respect to the longitudinal axis (see, FIG. 1B) of handle portion 301 so as to enable the probe 300a to be rotated about the longitudinal axis to various angular positions to position the probe for a procedure or measurement.

Also, shown in FIG. 3E is a probe cover 311d having a shaft 315 as can be attached to the probe by a slide on or an attachment mechanism in association with the attachment mechanism 312. For example, a groove in the probe shaft 319a or in association with the attachment mechanism 312 and a projection or engagement member 316 on or associated with the cover 311d allows the cover 311d and the probe shaft 319a to snap and engage together. The probe cover 311d has a tapered end 317, as can facilitate placing the cover on a curved probe shaft and can facilitate entry and positioning of the probe in the area of the body for radiation or magnetic activity detection, as described, according to the present invention. The arrow "J" indicates the placing of the cover 311d on the rod end portion 321a.

Figure 3F:
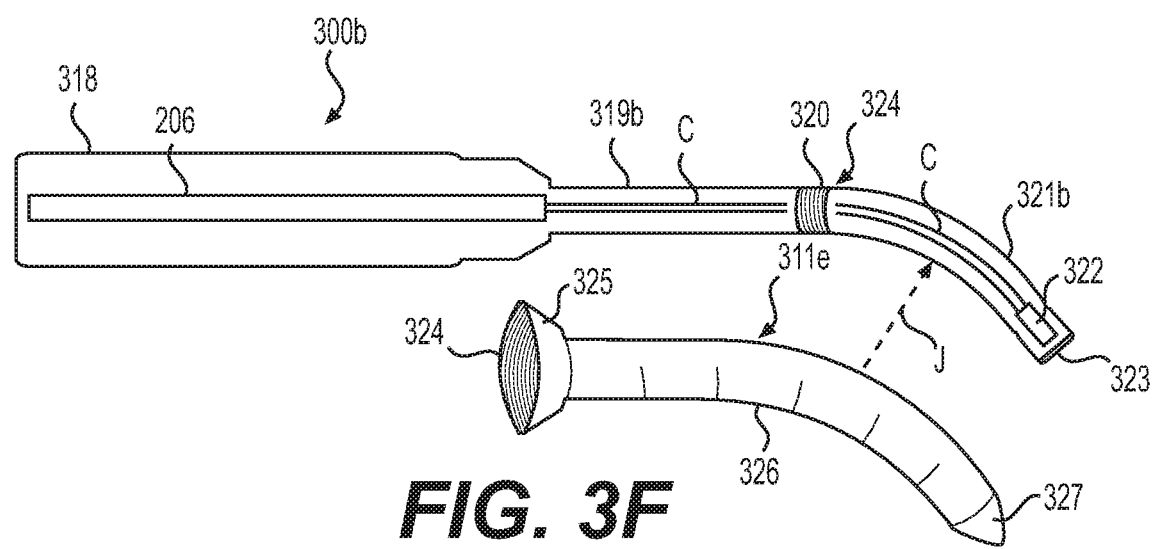
FIG. 3F shows a cross sectional view of an embodiment of an exemplary sterile detachable probe cover to be attached to a probe and an exemplary probe, as can have a fixed probe or detachable probe, such as the probes illustrated in FIGS. 1A and 3A, having the probe cover attached thereto, the probe cover being attached to the probe by a screw on type coupling mechanism, such as in FIGS. 3A and 3F, for example, according to the present invention.

FIG. 3F shows a transverse sectional view of an exemplary sterile detachable probe 300b, similar to the radioprobe 300 as described with respect to FIG. 3A. The probe 300b includes a handle portion 318, a shaft portion 319b in communication with the handle portion 318, and a curved rod probe portion 321b connected at 320 to the shaft portion 319b and a sensor or detector 323 similar to the sensor or detector 205, 305, as described with respect to FIGS. 2A, 2B and 3A to detect radiation or magnetic activity. The probe shaft portion 319b has the curved detachable rod portion probe 321b connected via an attachment mechanism 320, such as by a screw on type coupling 324. The curved rod detachable probe portion 321b can include one or more sensors or detectors 322, such as one or more metal-oxide-semiconductor field-effect transistors (MOSFETs) 205, 305 to detect the radiation or one or more magnetic resonance detectors or sensors 205, 305 to detect magnetic activity, as described with respect to FIGS. 2A, 2B and 3A, and provide radiation or magnetic activity detection information to the signal receiving and processing unit 206, via a wired or wireless communication channel or medium "C", to process or pre-process the detected radiation or magnetic activity information received from the sensor or detector 322. The curved rod detachable probe portion 321b can have a substantially linear configuration or a curved configuration, a curved configuration for the detachable probe portion 321b being illustrated in FIG. 3F, for example, The angle that is formed in and by the detachable rod probe portion 321b having a curved configuration can be suitably formed in an angular range of from about ten degrees (10°) to about 90 degrees (90°) or can be other suitable angle or curved configuration, as can depend on the use or application or a need to reach the vicinity of the implanted radioactivity seed, radioactive source or magnetic source in a body or a tissue of interest, for example. The curved rod detachable probe portion 321a can be configured to alter the angle of the tip thereof, such as from 10° to 90°, with respect to the longitudinal axis (see, FIG. 1B) of handle portion 318 so as to enable the probe 300b to be rotated about the longitudinal axis to various angular positions to position the probe for a procedure or measurement.

Also, shown in FIG. 3F is a probe cover 311e that has a shaft 326 that can be attached to the probe by a screw-on type coupling member 325 in association with the attachment mechanism 320. A mating engagement screw-on type coupling 324 on the probe shaft 319b or in association with the attachment mechanism 320 and in association with the screw-on type coupling member 325 allows the cover 311e and the probe shaft 321b to couple together such as by engaging threads of the screw-on type coupling 324 with corresponding threads of the screw-on type coupling 324 on the attachment mechanism 320. The probe cover 311e has a tapered end 327, as can facilitate placing the cover 311e on a curved probe shaft of the curved detachable rod probe portion 321b and can facilitate entry and positioning of the probe in the area of the body for radiation or magnetic activity detection, as described, according to the present invention. The arrow "J" indicates the placing of the cover 311e on the rod end portion 321b.

Figure 3G:
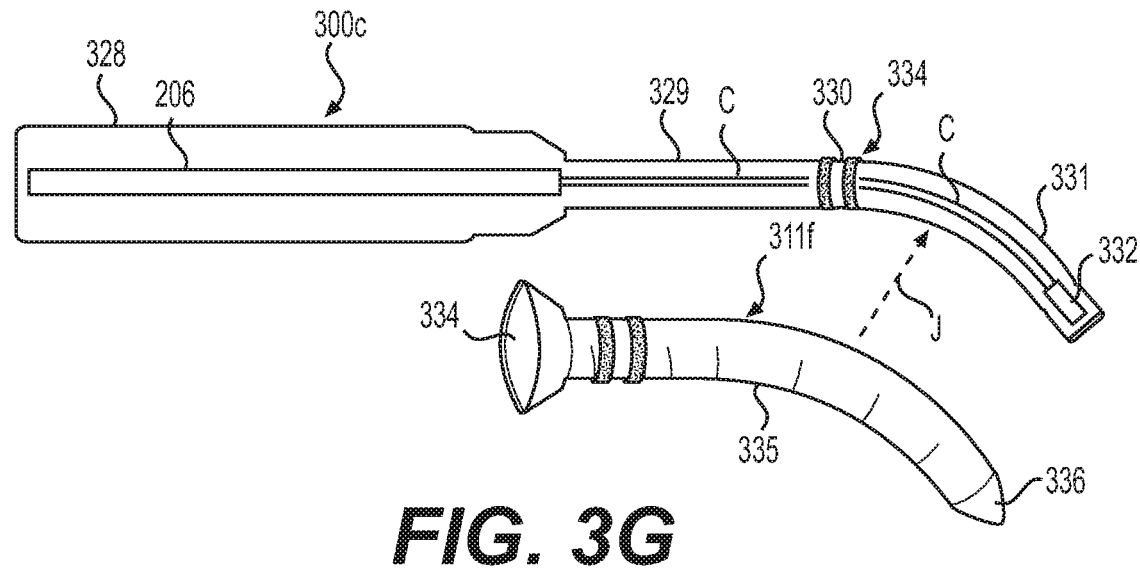
FIG. 3G shows a transverse sectional view of an embodiment of an exemplary sterile detachable probe cover to be attached to a probe and an exemplary probe, as can have a fixed probe or detachable probe, such as the probes illustrated in FIGS. 1A and 3A, having the probe cover attached thereto, the probe cover being attached to the probe by a quick fit coupling mechanism, according to the present invention.

FIG. 3G shows a transverse sectional view of an exemplary sterile detachable probe 300c, similar to the radioprobe 300 as described with respect to FIG. 3A. The probe 300c includes a handle portion 328, a shaft portion 329 in communication with the handle portion 328, and a detachable rod probe portion 331 connected at 330 to the shaft portion 329 and a sensor and detector 332 similar to the sensor or detector 205, 305, as described with respect to FIGS. 2A, 2B and 3A to detect radiation or magnetic activity. The probe shaft portion 329 has the detachable rod probe portion 331 connected via an attachment mechanism 330, such as by a quick fit coupling 330. The detachable rod probe portion 331 can include one or more sensors or detectors 332, such as one or more metal-oxide-semiconductor field-effect transistors (MOSFETs) 205, 305 to detect the radiation or one or more magnetic resonance detectors or sensors 205, 305 to detect magnetic activity, as described with respect to FIGS. 2A, 2B and 3A, and provide radiation or magnetic activity detection information to the signal receiving and processing unit 206, via a wired or wireless communication channel or medium "C", to process or pre-process the detected radiation or magnetic activity information received from the sensor or detector 332. The detachable rod probe portion 331 can have a substantially linear configuration or a curved configuration, and a curved configuration for the detachable rod probe portion 331 being illustrated in FIG. 3G, for example. The angle that is formed in and by the detachable rod probe portion 331 having a curved configuration can be suitably formed in an angular range of from about ten degrees (10°) to about 90 degrees (90°) or can be other suitable angle or curved configuration, as can depend on the use or application or as can depend on a need to reach the vicinity of the implanted radioactivity seed, radioactive source or magnetic source in a body or a tissue of interest. The detachable rod probe portion 331 can be configured to alter the angle of the tip thereof, such as from 10° to 90°, with respect to the longitudinal axis (see, FIG. 1B) of handle portion 328 so as to enable the probe 300c to be rotated about the longitudinal axis to various angular positions to position the probe for a procedure or measurement.

Also, shown in FIG. 3G is a probe cover 311f having a shaft 335 as can be attached to the probe by a quick fit coupling member 334 in association with the attachment mechanism 330. A mating engagement coupling member on the probe shaft 329 or in association with the attachment mechanism 330 allows the cover 311f and the detachable rod probe portion 331 to couple together. The probe cover 311f has a tapered end 336, as can facilitate placing the cover 311f on a detachable rod probe portion 331 and can facilitate entry and positioning of the probe 300c in the area of the body for radiation or magnetic activity detection, as described, according to the present invention. The arrow "J" indicates the placing of the cover 311f on the detachable rod probe portion 331.

FIG. 4A shows a perspective view of a radiation or magnetic activity detection system 400S and the various components of the detection system and the measurements and information related to the radiation or magnetic activity detection acquired, such as acquired from a handheld detection probe device 410. The handheld probe device 410 can be a probe, such as a gamma radioprobe or a magnetic resonance probe, for example, and the handheld probe device 410 can be the same as or similar to the probes described with respect to and illustrated in FIGS. 1A to 3G, for example. The handheld probe device 410 as part of the detection system 400S includes a handle portion 418 and a shaft portion 419 as includes the detectors and sensors 205, 305, as described, for example. The detection system 400S includes a communication medium, such as a wired cable, as can be used to transmit signals between the handheld radiation detection probe device 410 and a control unit 400, as a receiving device for the radiation or magnetic activity detection information. The control unit 400 can include various components for processing and displaying the radiation or magnetic activity detection information from the handheld radiation detection probe device 410. A transmitter/receiver 411, as can also be associated with the signal receiving and processing unit 206, can transmit and/or receive information from the control unit 400. In some embodiments, the communication medium in the detection system 400S can be a wireless connection medium 413, such as a RF wireless link, such as can include a Bluetooth communication medium for wireless communication with and to the control unit 400. The handheld radiation detection probe device 410 also can include an ON/OFF switch, button or indicator 405a, as described.

The control unit 400, as part of the detection system 400S, includes various components for receiving, processing, displaying and transmitting received radiation or magnetic activity detection information and the resultant analysis information, and can be displayed on a display meter or other representations or indications on the control unit 400. For example, in the control unit 400 a display meter 408 indicates the activity (counts) for the detected radiation, and the radioactivity counts can be plotted versus time on a graphical display 403, and/or the counts versus distance can be displayed on a graphical display 407. The type of isotopes detected can be displayed in an isotope display 409, and a total radiation count can be displayed in a total count display 404 of the control unit 400. Background radiation detected is displayed on a background radiation display 406. A power ON/OFF switch 405 can be included to selectively turn ON and turn OFF the control unit 400. Also, the various radioactivity displays 403, 404, 406, 407, 408 and 409, and other displays for displaying various information related to the radiation or magnetic activity detection process, as can be included on the display, can be provided and information therefor can be transmitted to a portable processing and display device 426, such as by wired or wireless communication 414, such as by Bluetooth or Wi-Fi communication, to a personal computer, a tablet, a cell phone device or a pad type processing/display device as the processing/display device 426, for example. The processing/display device 426, as a receiving device for the radiation or magnetic activity detection information, can include a remote controller 401 that can include associated processing circuitry and programs for the radiation or magnetic activity information processing, radiation or magnetic activity information display, radiation or magnetic activity information analysis, as well as can provide for control of the detection system 400S, such as to control the type of radiation or magnetic activity information to be received and the processing of that information, for example. The processing/display device 426 also can include a display device 402, as can be a touch pad type display device that can display the radiation or magnetic activity information and can control the radiation or magnetic activity information detection and processing. The processing/display device can be any of various suitable devices, such as a personal computer, a tablet, a cell phone device or a pad type processing/display device, for example.

FIG. 4B shows a schematic diagram and perspective view of the radiation or magnetic activity detection system 400S schematically illustrating various components for receiving, detecting and analyzing the radiation or magnetic activity detection information received from hand-held detection probe device 410 and for implementing display of the detected and processed radiation or magnetic activity information displayed via interfacing with other units, in embodiments of the present invention. As illustrated in FIG. 4B, the system 400S includes a controller/processor 422 as includes a processor for controlling and implementing the radiation or magnetic activity information detection, processing, display and transmission functions and operations, for those components, functions and operations previously described in relation to FIG. 4A. The controller/processor 422 is associated with a suitable memory 424 that includes storage for programs and data related to the operation and control of the system 400S and storage of the radiation or magnetic activity detection information and programs or software for the processing, display and transmission functions and operations of the detection system 400S, for example. The controller/processor 422 is in communication with a display 420 that is a suitable display for displaying the information discussed with respect to the displays and devices 403, 404, 406, 407, 408 and 409 or display of other radiation detection information or magnetic activity detection information. The controller/processor 422 is in communication with the hand-held radiation detection probe device 410 as indicated by communication medium 417, as can be a wired communication 417 or a wireless communication 416, for example. The controller/processor 422 in communication with display 420 can also display various types of magnetic activity information in various suitable formats on the display 420, as can be typically in formats or presentations known in the art, such as a suitable display of magnetic flux density, magnetic flux, magnetic field strength or magnetic field intensity in relation to a detected magnetic source in a tissue of interest, such as in relation to the diagnosis or treatment of cancer or disease, for example.

Continuing with reference to FIG. 4B, the controller/processor 422 is in communication with various processing units that perform various functions in the radiation or magnetic activity detection, information processing and reception and transmission of the radiation or magnetic activity detection information. For example, a radiation counter 423 is in communication with the controller/processor 422 to receive radiation detection information related to a radiation count to determine and provide radiation count information to display on the total count display 404 and to display the activity (counts) for the detected radiation on the display meter 408. Also, for example, a background analyzer 425 is in communication with the controller/processor 422 to receive radiation detection information related to background radiation detected and to process and provide background radiation information to display on the background radiation display 406. The controller/processor 422 is in communication with an interface/user interface 429 for inputting/receiving and communicating information and control commands in the detection system 400S. A receiver/transmitter 427 is communicatively connected with the controller/processor 422, such as through the interface/user interface 429, to transmit and receive radiation or magnetic activity detection information and to transmit and receive control commands for the system 400S operation, such as to/from the remote device 426, by wired or wireless communication, as described. An isotope multichannel analyzer 430 is in communication with the controller/processor 422 to receive radiation detection information related to identifying isotopes detected and to process and provide isotope detection information to display on the isotope display 409.

The detection system 400S can include a power ON/OFF control 428 connected with a power source 431, such as a wired or a battery powered source, for powering the detection system 400S, the power ON/OFF switch being communicatively connected with the controller/processor 422, such as through the interface/user interface 429, to selectively control the power to and the on/off state of the system 400S. As described with respect to FIGS. 4A and 4B above, the hand-held detection probe device 410 can be wired directly by a communication medium 417 for physically connecting data communication wire 412 to the controller/processor unit 422. Also, the handheld detection probe device 410 can communicate with an external device using one or more wireless communication links 413 or 414. For example, Bluetooth Low Energy (BLE) circuitry can be used to enable a low cost, battery driven wireless link to an external probe system control and display unit in a cell phone 500 or other computing devices, such as a laptop computer 510 (FIGS. 5A and 5B) for exchanging data and/or commands with the control unit 400 and with the handheld detection probe device 410. Other examples of wireless connectivity include various families of Wi-Fi technologies. Examples of the computing devices capable of wirelessly communicating with the handheld detection probe device 410, such as a gamma radioprobe or a magnetic resonance probe, include portable computing devices, such as a tablet, a computer, the laptop 510, the cell phone 500, such as a smart phone, etc.

FIGS. 4A and 4B illustrate a generalized detection system 400S for receiving, transmitting and processing radiation or magnetic activity detection information, although it should be understood that the generalized detection system 400S may represent, for example, a stand-alone computer, computer terminal, portable computing device, networked computer or computer terminal, or networked portable device. Data may be entered into the detection system 400S by the user via any suitable type of user interface 429, and may be stored in computer readable memory as the memory 424, which may be any suitable type of computer readable and programmable memory. Calculations are performed by the controller/processor 422, and also the processing operations of the various described components of the system 400S, which may be any suitable type of computer processor, and may be displayed to the user on the display 420 of the control unit 400 or on the device 426, which may be any suitable type of computer display, for example.

Examples of computer readable media include a magnetic recording apparatus, non-transitory computer readable storage memory, an optical disk, a magneto-optical disk, and/or a semiconductor memory (for example, RAM, ROM, etc.). Examples of magnetic recording apparatus that may be used in addition to memory 424, or in place of memory 424, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Figure 5A:
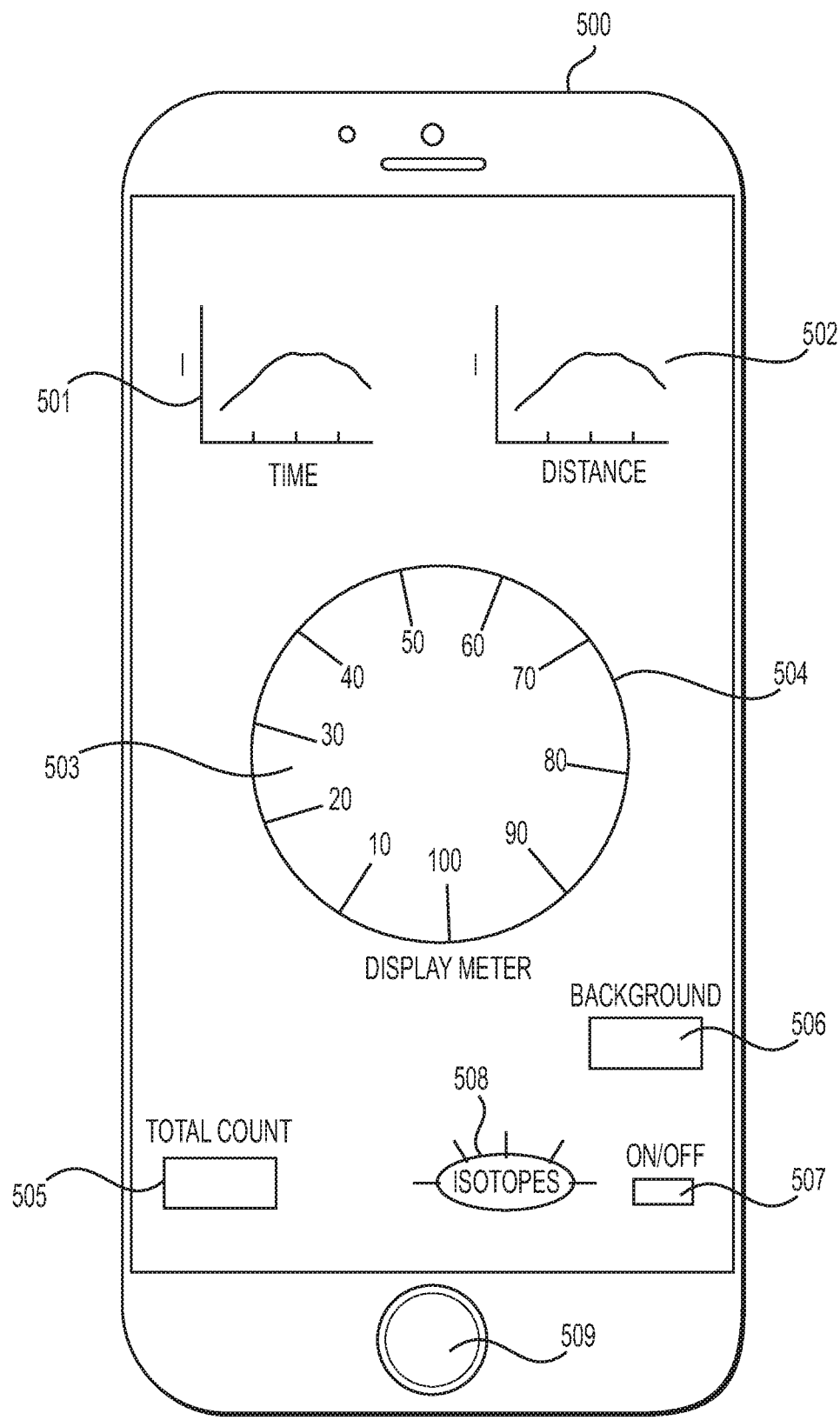
FIG. 5A shows a perspective view of an embodiment of the radiation measurement displayed on a cell phone device, according to the present invention.

For example, FIG. 5A shows the radioactivity display on the cell phone device 500. Bluetooth Low Energy (BLE) circuitry can be used to enable a low cost, battery driven wireless link to the external cell phone device 500. The cell phone device 500 can be turned on or off using a switch 509. As shown by the graph 501, the radioactivity intensity (I) can be plotted versus time (t) on a small display system or the intensity (I) can be plotted as a function of the distance (d) of the probe as shown by the display graph 502 to the site of the radioactivity implant. The radio measurement application software switch 507 can be turned on to measure the radiation emitted from the various radio isotopes 508 such as for example from the radioisotopes $^{125}$I, $^{131}$I, $^{99m}$Tc, $^{103}$Pd, $^{111}$In, $^{90}$Y, $^{153}$Sm, etc. The display meter 504 can have a dial 503 showing the amount of radiation measured and there can be a display counter 506 for the background noise and the total count counter 505 to provide a ratio of the radiation activity to correct for accuracy, etc. in performing the measurement and analysis of the radiation detection information, for example. The cell phone device 500 can also display various types of magnetic activity information in various suitable formats on its display, as can be typically in formats or presentations known in the art, such as a suitable display of magnetic flux density, magnetic flux, magnetic field strength or magnetic field intensity in relation to a detected magnetic source in a tissue of interest, such as in relation to the diagnosis or treatment of cancer or disease, for example.

Figure 5B:
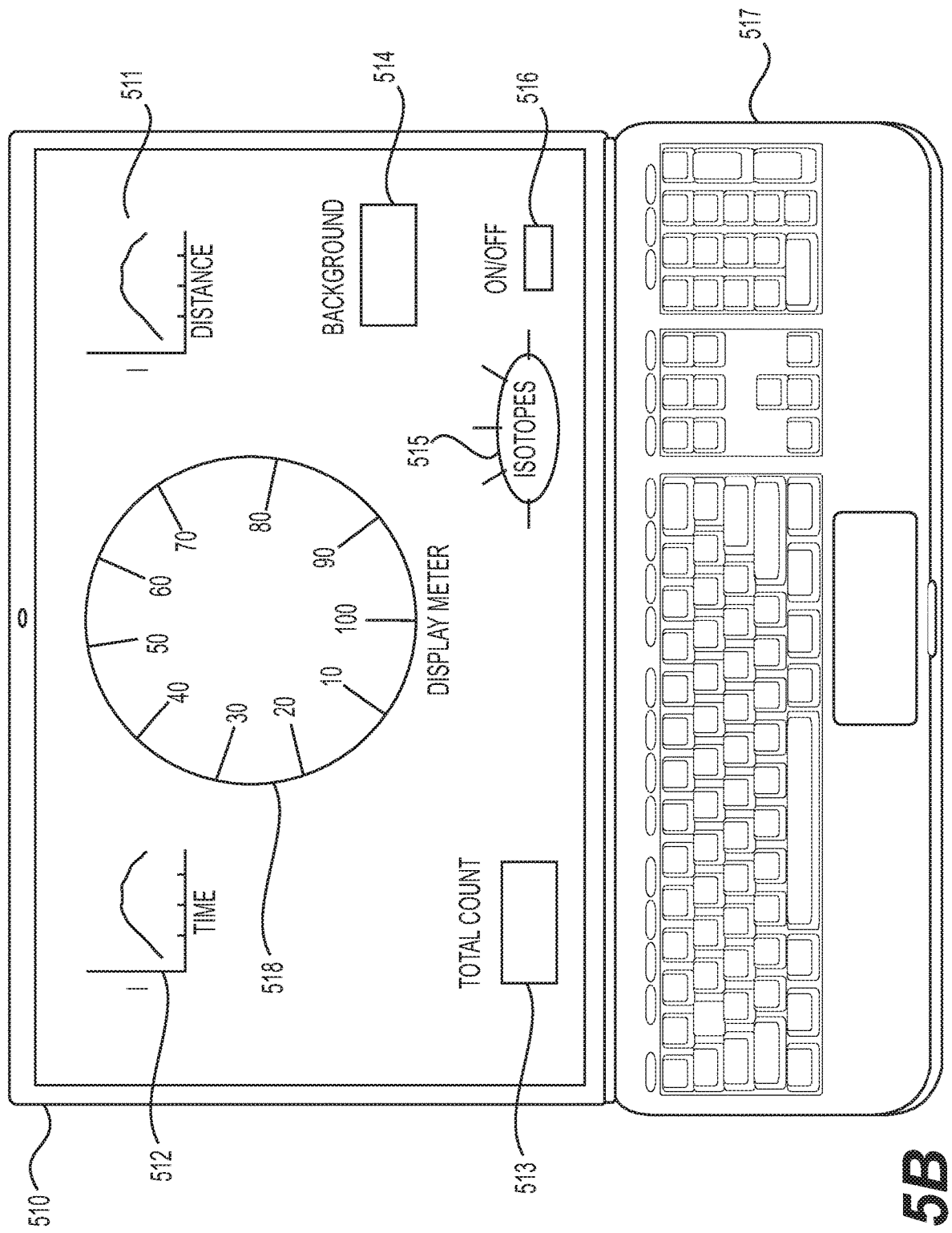
FIG. 5B shows a perspective view of an embodiment of the radiation count displayed on a laptop computer device, according to the present invention.

FIG. 5B shows the radioactivity display on a computer, such as on a lap top computer 510. As discussed above for FIG. 5A, Bluetooth Low Energy (BLE) circuitry can be used to enable a low cost, battery driven wireless link to an external portable computing device, such as the lap-top computer 510 having a keyboard 517, for example. For example, as shown on the graph 512 on a display of the lap top computer 510, the radioactivity intensity (I) can be plotted versus time (t) or, as shown on the display of the lap top computer 510, the radioactivity intensity (I) can be plotted as a function of the distance (d) of the probe to the site of the radioactivity implant as shown by the plot 511. The radioactivity measurement application/software switch 516 on the display of the lap top computer 510 can be turned on to measure the radiation emitted from the various isotopes and display the measurement results on an isotope display 515. A display meter 518 on the display of the lap top computer 510 can have a dial showing the amount of radiation measured, as illustrated in FIG. 5B and, on the display of the lap top computer 510, there can be a display counter meter 514 for measuring and displaying the background noise count and there can also be a total actual count meter 513 to measure and display the actual radiation count from the radiation source to provide a ratio of the radioactivity in order to correct for accuracy during the radiation measurement, for example. The lap top computer 510 can also display various types of magnetic activity information in various suitable formats on its display, as can be typically in formats or presentations known in the art, such as a suitable display of magnetic flux density, magnetic flux, magnetic field strength or magnetic field intensity in relation to a detected magnetic source in a tissue of interest, such as in relation to the diagnosis or treatment of cancer or disease, for example.

Figure 6B:
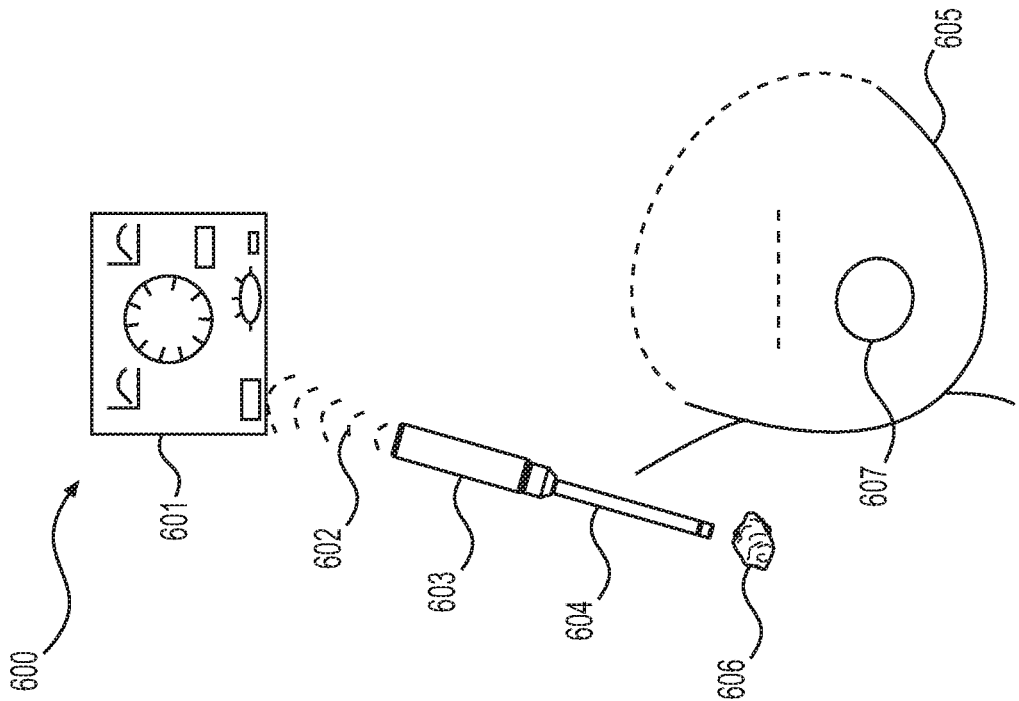
FIG. 6B shows a diagram illustrating a perspective view of an embodiment of a radioprobe radiation detection system illustrating the radioprobe measuring the radiation in the vicinity (ex-vivo) outside of the female human breast, according to the present invention.
Figure 6A:
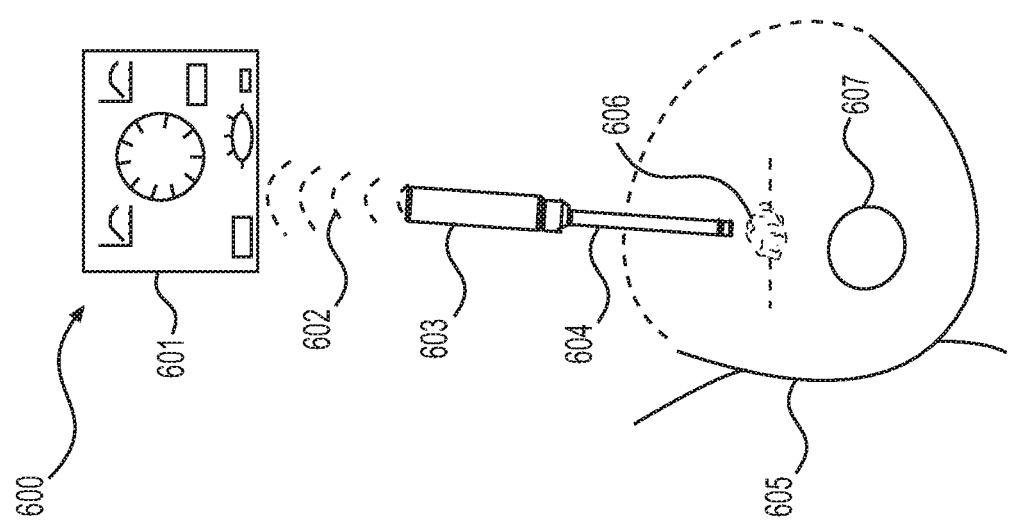
FIG. 6A shows a perspective view of an embodiment of a radioprobe radiation detection system illustrating the radioprobe measuring the radiation of the implant inside (in vivo) of a female human breast, according to the present invention.

FIG. 6A shows an example of a radioprobe, such as a probe being a radioprobe illustrated and described in relation to FIGS. 2A, 2B and 3A-3G, measuring the radiation from an implant 606 inside a female human breast 605 (in vivo), in a detection system 600, similar to the detection system 400S as described in relation to FIGS. 4A and 4B. The radioprobe with the handle 603 having the shaft 604 is inserted surgically into the breast 605 and it is placed in the vicinity of the implant 606 inside the breast 605 having a nipple 607 thereon. The detected radiation data can be transmitted by a wireless mechanism 602 to a data receiver/processor 601 of the detection system 600 to further process and display the radiation intensity data or information, such as previously described in relation to the system 400S, for example.

FIG. 6B shows an example of the radioprobe, such as a probe being a radioprobes illustrated and described in relation to FIGS. 2A, 2B and 3A-3G, measuring the radiation in the vicinity (Ex vivo) outside of the female breast 605, in the detection system 600, similar to the detection system 400S as described in relation to FIGS. 4A and 4B. The radioprobe 603 having a probe shaft 604 can be used or placed outside near the surface of the human breast 605 having the nipple 607 thereon. The detected radiation data can be transmitted by the wireless mechanism 602 to the data receiver/processor 601 to further process and display the radiation intensity data or information, such as previously described in relation to the system 400S, for example. In the embodiment of FIG. 6B, there is depicted the use of the radioprobe to qualitatively and quantitatively determine the presence and intensity of radiation from a tissue of interest (tumor, nodes, infectious foci, etc.) once the tissue is dissected and placed outside a patient's body (ex-vivo).

Use of the described methods, systems and apparatuses of embodiments of exemplary probes, radiation or magnetic activity detection systems, and methods for detecting radiation or magnetic activity around a radiation source or magnetic source near a tumor target or other diseased tissue or near tissue or an organism of interest can facilitate providing a practitioner, such as a surgeon, a relatively expedient indication and determination as to whether the practitioner has removed all the tissue of interest (such as in the Operating Room), for example. In contrast, a pathology lab test for such determination typically can take up to a week for the results. Additionally, embodiments of the probe can also be intraoperatively inserted into a surgical cavity and/or intracavitary spacing existing in the body to determine the presence and intensity of radiation or magnetic activity.

EXAMPLE 1

Method of Detecting Radiation Using a Target

In an example of an embodiment of a method for detecting radiation, a subject is injected with a radiation emitting source, such as an implantable seed or radioactivity producing nuclei as, for example, $^{125}$I, $^{131}$I, $^{99m}$Tc, $^{103}$Pd, $^{111}$In, $^{90}$Y, $^{153}$Sm, etc. in order to treat a tumor, such as in the breast or prostrate. After sufficient time has elapsed for accumulation of the radiation source into the target cancerous tissue (tumor, infection, antigen present areas, sentinel nodes, etc.) the radioprobe can be inserted into the site of the tumor to acquire radiation information and quantitate the presence of radioactivity.

Figure 7:
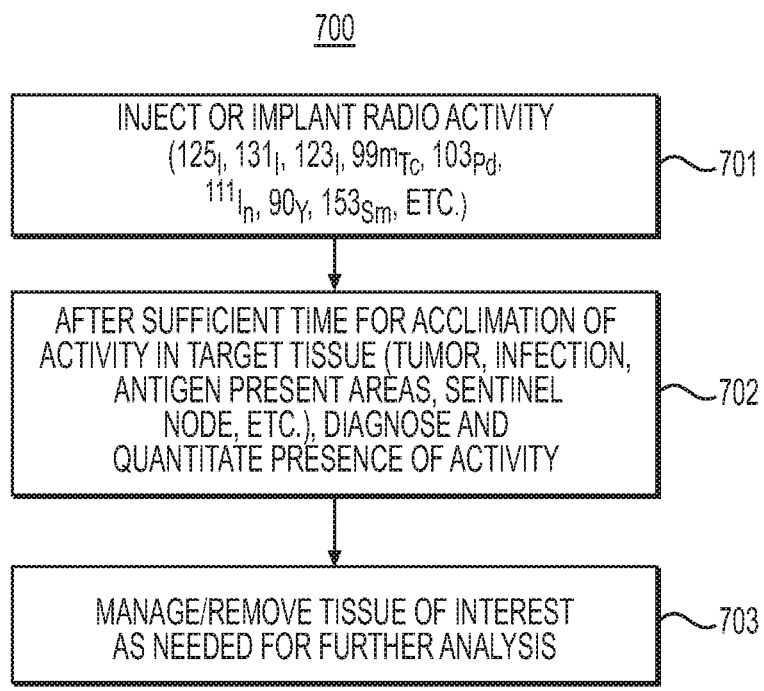
FIG. 7 is a flow chart for an exemplary embodiment of a process for measuring radiation in an area of interest in a body by an embodiment of a radioprobe in a radiation detection system, according to the present invention.

Referring now to FIG. 7, there is illustrated a flow chart for an exemplary embodiment of a process for measuring radiation in an area of interest in a body by an embodiment of a radioprobe in a radioprobe radiation detection system according to the present invention.

Initially, in step 701, a radiation emitting source, such as a radioactive label, is either implanted or injected into a subject. The radioisotopes, such as for the radioactive label, can be $^{125}$I, $^{131}$I, $^{123}$I, $^{99m}$Tc, $^{103}$Pd, $^{90}$Y, $^{153}$Sm, $^{111}$In, etc., for example. In step 702, after sufficient time for accumulation of radioactive activity has elapsed in a target tissue, such as tumor, infection antigen present area, sentinel node, etc., the radioprobe is used to diagnose and quantitate the presence of the radioactive activity. Once the target tissue has been detected and quantitated for radioactivity, the tissue of interest can be removed and managed as needed for further analysis in the final step 703.

Also, embodiments of methods for detecting radiation around a radiation source or detecting magnetic activity around a magnetic source near a tumor target or other diseased tissue or near an organism or tissue of interest are provided including the steps of: identifying a tumor in a target tissue or a tissue of interest organ to be treated in a patient; disposing an implantable radioactive seed, a radioactive material or compound, or a magnetic particle-containing source, such as a magnetic particle-containing marker or compound, at the location near said tumor, target tissue, tissue of interest or organ; inserting a probe near the proximity of the seed, compound or marker; measuring the radioactivity or magnetic activity from the source, seed, compound or marker, such as based on a distance of the probe to the seed, compound or marker; transmitting radioactivity data or magnetic activity data from the measurement to a data processor by wireless or wired communication, such as by a cable attached to the radio-probe; quantifying the radioactivity or magnetic activity near the tumor, target tissue, tissue of interest or organ; displaying at least one indication of the detected radiation or magnetic activity on a display device to determine a status of the tumor, target tissue, tissue of interest or organ tumor, target tissue, tissue of interest or organ to diagnose or treat cancer or a disease, such as to determine the status of the sentinel lymph nodes in relation to the measured radioactivity or magnetic activity and the marker.

Embodiments of measuring radiation from a radioactive source or magnetic activity form a magnetic source, such as magnetic activity from a magnetic particle-containing marker or compound, using embodiments of a probe detection device, can also include quantifying the radioactivity or magnetic activity near the tumor or tissue of interest, such as by quantifying the radiation detection information as, for example, by plotting the counts versus time or the counts versus distance information, or by quantifying the magnetic activity information by suitably displaying magnetic activity information, such as magnetic flux density, magnetic flux, magnetic field strength or magnetic field intensity in relation to a detected magnetic source. Also, in embodiments, the data processor can be a cell phone or a laptop computer, or other suitable device that communicates with the probe detection device, such as by wired or wireless communication. Embodiments of methods for measuring radiation or magnetic activity using a probe detection device, such as a radioprobe or a magnetic resonance probe, can further include removing tissue of interest for further analysis as, for example, can include, but is not limited to, the process described with respect to FIG. 6B.

In exemplary embodiments, methods of measuring the radiation or magnetic activity from the implant can be extended to include animals, reptiles and other living organisms, but is not limited thereto, as can depend on the use or application, for example.

It is to be understood that the present invention is not limited to the embodiments described above, but encompasses any and all embodiments within the scope of the following claims.

We claim:

1. A hand-held radioprobe for measuring radiation, comprising:
a probe including a handle having a longitudinal axis and a substantially elongated shaft portion fixed to and extending from the handle, the shaft portion being adapted to be inserted into a cavity of a body or held above a tissue of interest to detect radiation emitted from a radiation emitting source implanted within the body or in the tissue of interest;

at least one radiation sensor associated with the shaft portion configured to detect and measure the radiation emitted from the radiation emitting source, the shaft portion having a substantially straight portion, an attachment mechanism at a distal end of the substantially straight portion and a detachable probe portion rotatable about the longitudinal axis of the handle and with respect to the substantially straight portion to selectively rotate the probe portion into a plurality of predetermined angular positions about the longitudinal axis to position the probe for detecting and measuring the radiation emitted from the radiation emitting source, the detachable probe portion having a proximal end detachably coupled to the attachment mechanism and rotatable thereon into the plurality of predetermined angular positions;

a substantially elongated sterile probe cover detachably mounted over the shaft portion;

a signal processing device associated with the radioprobe for processing data for the detected and measured radiation emitted from the radiation emitting source; and a communication medium associated with the radioprobe to provide the processed data for the detected and measured radiation emitted from the radiation emitting source from the signal processing device to a receiving device associated with an external data processor unit for processing and selectively displaying radiation detection information corresponding to the received processed data for the detected and measured radiation emitted from the radiation emitting source.

2. The hand-held radioprobe for measuring radiation according to claim 1, wherein:

the shaft portion comprises a plurality of radiation sensors placed inside of the shaft portion for selectively detecting gamma radiation.

3. The hand-held radioprobe for measuring radiation according to claim 1, wherein:

the shaft portion has a length of 5 cm to 210 cm.

4. The hand-held radioprobe for measuring radiation according to claim 1, wherein:

the shaft portion has a thickness of 1 mm to 5 cm.

5. The hand-held radioprobe for measuring radiation according to claim 1, wherein the communication medium comprises:

a data communication medium to transmit the processed data for the detected and measured radiation emitted from the radiation emitting source to a computer, a laptop computer, a tablet, or a cell phone device as the receiving device associated with the external data processor unit.

6. The hand-held radioprobe for measuring radiation according to claim 1, wherein:

the communication medium is a direct-coupled wired or a wireless communication medium.

7. The hand-held radioprobe for measuring radiation according to claim 1, further comprising:

a power supply device for powering the at least one radiation sensor, the signal processing device and the communication medium.

8. The hand-held radioprobe for measuring radiation according to claim 1, wherein:

the at least one radiation sensor is a metal-oxide-semiconductor field-effect transistor (MOSFET) sensor or a semiconductor diode or a scintillation counter.

9. The hand-held radioprobe for measuring radiation according to claim 1, wherein:

the detachable probe portion comprises a detachable curved probe portion configured to angle a tip of the probe in a range of from ten degrees (10°) to ninety degrees (90°) with respect to the longitudinal axis of the handle and adapted to be selectively rotated about the longitudinal axis into the plurality of predetermined angular positions to position the probe for detecting and measuring the radiation emitted from the radiation emitting source.

10. The hand-held radioprobe for measuring radiation according to claim 1, wherein:

the communication medium of the radioprobe communicates with the receiving device to provide information associated with an intensity of the radiation emitting source.

11. The hand-held radioprobe for measuring radiation according to claim 1, wherein:

the radiation emitting source produces radiation emissions selected from the group consisting of alpha rays, beta rays, gamma rays, x rays, and neutrons.

12. The hand-held radioprobe for measuring radiation according to claim 1, wherein:

the shaft portion of the probe includes a housing material selected from the group consisting of a polymeric material, glass, silicone, stainless steel, tungsten, copper, titanium and an alloy thereof.

13. A probe, comprising:

a handle having a longitudinal axis and a substantially elongated shaft portion fixed to and extending from the handle, the shaft portion being adapted to be inserted into a cavity of a body or held above a tissue of interest to detect radiation emitted from a radiation emitting source or to detect magnetic activity from a magnetic emitting source implanted within the body or in the tissue of interest, the shaft portion having a substantially straight portion, an attachment mechanism at a distal end of the substantially straight portion and a detachable probe portion rotatable about the longitudinal axis of the handle and with respect to the substantially straight portion to selectively rotate the probe portion into a plurality of predetermined angular positions about the longitudinal axis to position the probe for detecting and measuring the radiation emitted from the radiation emitting source or for detecting and measuring the magnetic activity from the magnetic emitting source, the detachable probe portion having a proximal end detachably coupled to the attachment mechanism and rotatable thereon into the plurality of predetermined angular positions;

at least one sensor associated with the shaft portion configured to detect and measure the radiation emitted from the radiation emitting source or to detect and measure the magnetic activity from the magnetic emitting source;

a substantially elongated sterile probe cover detachably mounted over the shaft portion;

a signal processing device for processing data for the detected and measured radiation emitted from the radiation emitting source or for the detected and measured magnetic activity from the magnetic emitting source; and a communication medium associated with the probe to provide the processed data for the detected and measured radiation emitted from the radiation emitting source or to provide the processed data for the detected and measured magnetic activity from the magnetic emitting source from the signal processing device to a receiving device associated with an external data processor unit, the external data processor unit for processing and selectively displaying radiation detection information corresponding to the received processed data for the detected and measured radiation emitted from the radiation emitting source or for processing and selectively displaying magnetic activity information corresponding to the received processed data for the detected and measured magnetic activity from the magnetic emitting source.

14. A detection system for detecting radiation or magnetic activity, comprising:

a probe, the probe adapted to be inserted into a cavity of a body or held above a tissue of interest to detect radiation emitted from a radiation emitting source or to detect magnetic activity from a magnetic emitting source implanted within the body or in the tissue of interest, the probe having a longitudinal axis and a shaft portion fixed to a handle, the shaft portion having a substantially straight portion, an attachment mechanism at a distal end of the substantially straight portion and a detachable probe portion rotatable about the longitudinal axis and with respect to the substantially straight portion to selectively rotate the probe portion into a plurality of predetermined angular positions about the longitudinal axis to position the probe for detecting and measuring the radiation emitted from the radiation emitting source or for detecting and measuring the magnetic activity from the magnetic emitting source, the detachable probe portion having a proximal end detachably coupled to the attachment mechanism and rotatable thereon into the plurality of predetermined angular positions;

at least one sensor associated with the shaft portion to detect and measure the radiation emitted from the radiation emitting source or to detect and measure the magnetic activity from the magnetic emitting source;

a sterile probe cover detachably mounted over the shaft portion;

a signal processing device associated with the probe for processing data for the detected and measured radiation emitted from the radiation emitting source or for the detected and measured magnetic activity from the magnetic emitting source; and a communication medium associated with the probe to provide the processed data for the detected and measured radiation emitted from the radiation emitting source or to provide the processed data for the detected and measured magnetic activity from the magnetic emitting source from the signal processing device to a receiving device associated with an external data processor unit for processing and selectively displaying radiation detection information corresponding to the received processed data for the detected and measured radiation emitted from the radiation emitting source or for processing and selectively displaying magnetic activity information corresponding to the received processed data for the detected and measured magnetic activity from the magnetic emitting source.

15. The detection system for detecting radiation or magnetic activity according to claim 14, further comprising:

the receiving device for receiving from the communication medium the processed data for the detected and measured radiation emitted from the radiation emitting source or for receiving from the communication medium the processed data for the detected and measured magnetic activity from the magnetic emitting source from the signal processing device;

the external data processor unit associated with the receiving device for processing the received processed data for the detected and measured radiation emitted from the radiation emitting source to provide the radiation detection information or for processing the received processed data for the detected and measured magnetic activity from the magnetic emitting source to provide the magnetic activity information; and a display device associated with the external data processor unit to selectively display the radiation detection information or to selectively display the magnetic activity information.

16. The detection system for detecting radiation or magnetic activity according to claim 15, wherein:

the receiving device and the external data processor unit comprise a computer, a laptop computer, a tablet, or a cell phone device.

17. A method for measuring radiation or magnetic activity, comprising the steps of:

identifying a target tissue of interest;

disposing a radiation emitting source or a magnetic emitting source at a location corresponding to the target tissue of interest;

positioning a probe in proximity to the radiation emitting source or in proximity to the magnetic emitting source, the probe adapted to be inserted into a cavity of a body or held above the target tissue of interest to detect radiation emitted from the radiation emitting source or to detect magnetic activity from the magnetic emitting source, the probe having a shaft portion fixed to a handle, a longitudinal axis and a sterile probe cover detachably mounted over the shaft portion, the shaft portion having a substantially straight portion, an attachment mechanism at a distal end of the substantially straight portion and a detachable probe portion rotatable about the longitudinal axis and with respect to the substantially straight portion to selectively rotate the probe portion into a plurality of predetermined angular positions about the longitudinal axis to position the probe for detecting and measuring the radiation emitted from the radiation emitting source or for detecting and measuring the magnetic activity from the magnetic emitting source, the detachable probe portion having a proximal end detachably coupled to the attachment mechanism and rotatable thereon into the plurality of predetermined angular positions;

measuring radioactivity from the radiation emitted from radiation emitting source or measuring the magnetic activity from the magnetic emitting source based on a distance of the probe from the radiation emitting source or from the magnetic emitting source;

transmitting from the probe radioactivity data corresponding to the measurement of the radioactivity or transmitting from the probe magnetic activity data corresponding to the measurement of the magnetic activity to a data processor by wired or wireless communication;

processing by the data processor the received radioactivity data to provide radiation detection information or processing by the data processor the received magnetic activity data to provide magnetic activity information; and selectively displaying by a display device associated with the data processor the radiation detection information or the magnetic activity information.

18. The method for measuring radiation or magnetic activity according to claim 17, further comprising the steps of:
quantifying by the data processor the received radioactivity data to provide the radiation detection information corresponding to one or more of counts versus time or counts versus distance; and
displaying on the display device the quantified counts versus time or the counts versus distance.

19. The method for measuring radiation or magnetic activity according to claim 17, further comprising the steps of:
quantifying by the data processor the received magnetic activity data to provide the magnetic activity information corresponding to one or more of magnetic flux density, magnetic flux, magnetic field strength, or magnetic field intensity in relation to the measurement of the magnetic activity from the magnetic emitting source; and
displaying on the display device one or more of the quantified magnetic flux density, magnetic flux, magnetic field strength, or magnetic field intensity.

20. The method for measuring radiation or magnetic activity according to claim 17, wherein:
the data processor is a cell phone, a computer, a laptop computer, or a tablet.

21. The method for measuring radiation or magnetic activity according to claim 17, further comprising the step of:
removing the target tissue of interest from the body to measure the radioactivity of the radiation emitted from the radiation emitting source or to measure the magnetic activity from the magnetic emitting source.

* * * * *